United States Patent [19]

Suciu et al.

[11] Patent Number: 4,857,151
[45] Date of Patent: Aug. 15, 1989

[54] PHENOL PURIFICATION

[75] Inventors: George D. Suciu, Ridgewood; Ali M. Khonsari, Bloomfield; Jamin Chen, Montville, all of N.J.

[73] Assignee: The Lummus Company, Bloomfield, N.J.

[21] Appl. No.: 392,569

[22] Filed: Jun. 28, 1982

[51] Int. Cl.⁴ .......................... B01D 3/36; C07C 37/78
[52] U.S. Cl. .......................... 203/82; 203/39; 203/83; 568/749; 568/754
[58] Field of Search ............. 203/83, 76, 74, 75, 203/77, 81, 82, 96, 95, 97, 92, 93, 39; 568/749, 754

[56] References Cited

U.S. PATENT DOCUMENTS

| | | | |
|---|---|---|---|
| 2,344,791 | 3/1944 | Stoesser | 203/97 |
| 2,573,244 | 10/1951 | Bogart et al. | 203/76 |
| 2,862,855 | 12/1958 | Lang et al. | 203/97 |
| 2,927,064 | 3/1960 | Luzader et al. | 203/76 |
| 2,971,893 | 2/1961 | Hood | 203/83 |
| 3,029,293 | 4/1962 | Nixon | 568/754 |
| 3,298,933 | 1/1967 | Prahl et al. | 203/39 |
| 3,335,070 | 8/1967 | Adams | 203/83 |
| 4,298,765 | 11/1981 | Cochran et al. | 568/754 |
| 4,351,967 | 9/1982 | Nishimura et al. | 568/754 |

Primary Examiner—Wilbur Bascomb
Attorney, Agent, or Firm—Elliot M. Olstein

[57] ABSTRACT

Crude phenol containing methyl benzofuran and other impurities is distilled in the presence of water to recover a phenol bottoms having a reduced quantity of impurities. The water-phenol overhead is cooled to separate a water phase essentially free of methyl benzofuran, which is recycled to the distillation. The organic phase may then be further distilled, in the presence of water, as previously described, to eventually recover a reduced quantity of phenol in which impurities are concentrated.

5 Claims, 1 Drawing Sheet

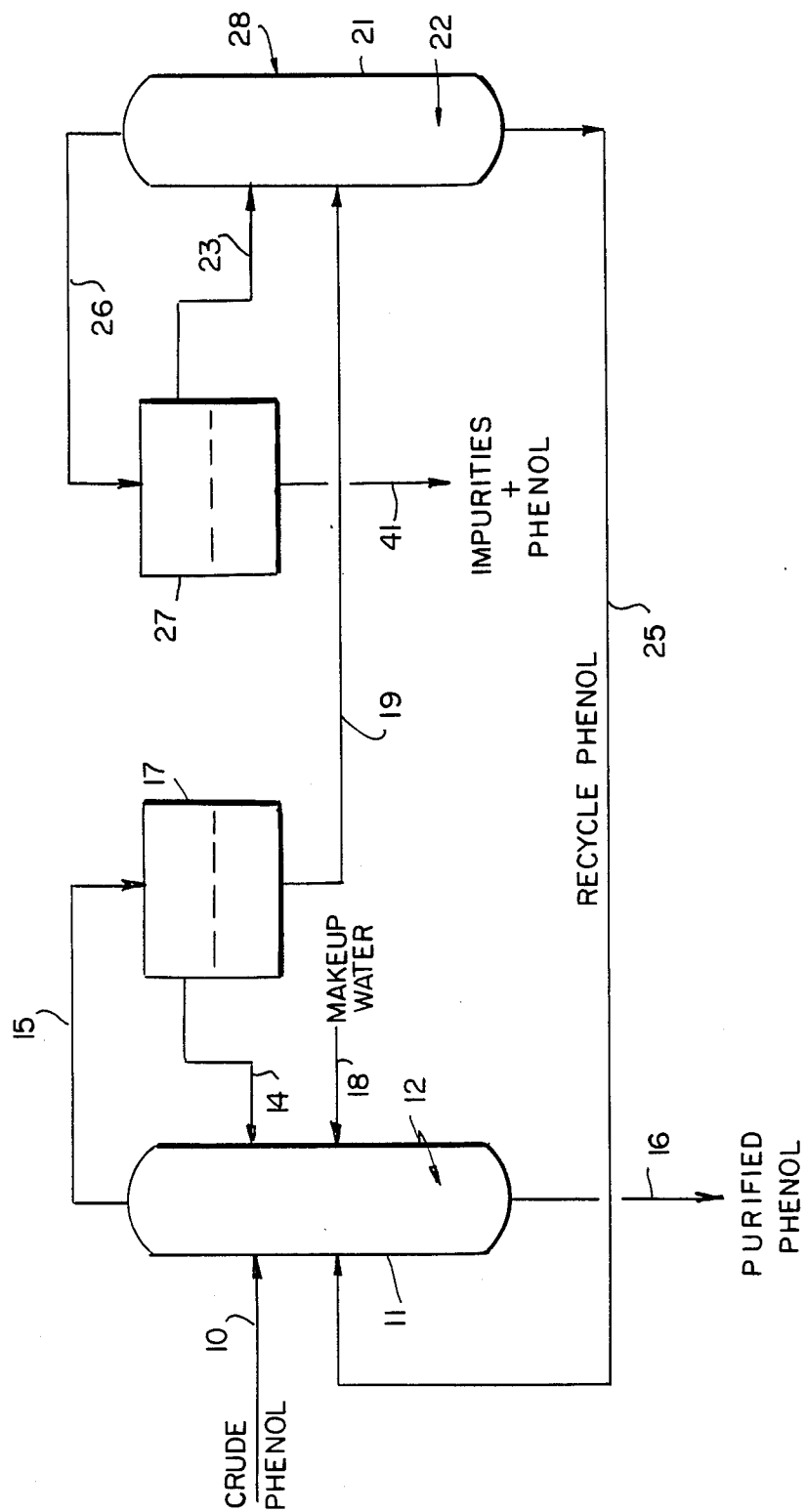

PHENOL PURIFICATION

This invention relates to the production of phenol, and more particularly to the production of high purity phenol.

In the production of high purity phenol, crude phenol obtained, for example, by the oxidation of cumene to cumene hydroperoxide, and acid cleavage of such hydroperoxide to phenol and acetone, followed by recovery of a crude phenol, is further purified to remove impurities such as acetol, mesityl oxide, acetophenone, 2-and 3-methyl benzofuran (individually or collectively emthyl benzofuran or MBF), etc.

In one such process, the crude phenol is treated with an amine, followed by the addition of acid or acid anhyudride and distillation to recover high purity phenol, with such a procedure being disclosed in U.S. Pat. No. 3,692,845. U.S. Pat. No. 4,298,765 describes an improvement over such a procedure, wherein, after treatment with base, and optionally an acid or acid anhydride, the treated phenol is distilled in the presence of water to recover from the top of the column a phenol-water azeotrope which also contains the majority of the MBF and other impurities, initially present in the treated phenol. Water present in the azeotrope is treated to separate MBF and other impurities so as to enable recycle of such water to the distillation.

In accordance with the aforesaid patent, after an initial separation from a phenol phase, the water in the overhead is treated, with a solvent to extract organics therefrom, or the phenol-water mixture is treated with a solvent, followed by phase separation of organics. In such a process, a significant portion of the phenol present in the overhead is recovered in the organic phase, and it is then necessary to separately treat such organic phase to recover such significant portion of phenol. Such recovery increases overall costs.

In accordance with the present invention, crude phenol, containing MBF, and other impurities is distilled in the presence of water to recover, as overhead product a mixture of phenol and water, which also contains the majority of MBF and other impurities which are initially present in the feed to the distillation, and as bottoms product a phenol fraction having a reduced quantity of MBF. Upon condensing and cooling the overhead stream, an organic phase and an aqueous phase are separately recovered from the phenol-water mixture, with such aqueous phase being essentially free of MBF. Accordingly, such water phase may be recycled to the distillation.

The organic phase, which is comprised of phenol, some dissolved water, MBF and other impurities, is then distilled in the presence of additional water to recover as bottoms product a phenol stream which is suitable for recycle (as feed) to the initial distillation, and an overhead product comprised of a phenol-water mixture which also contains the majority of MBF and other impurities which were initially present in the feed to the distillation which, upon condensation and cooling, is separated into an organic phase and an aqueous phase, with such aqueous phase being suitable for recycle as feed to one or both of the prior distillations.

The organic phase in the second distillation overhead is comprised mainly of phenol in which MBF and other impurities are concentrated with such phenol overhead being a very small portion of the total phenol feed to the first distillation. Such phenol may be further treated for phenol recovery. Such treatment may be a further distillation in the presence of water or a series of chemical treatments where phenol is reacted with base to convert phenol to water soluble phenate, while MBF and other impurities remain as a separate organic phase. After phase separation, the aqueous phenate is purified and acidified to regenerate phenol. Since the phenol in this organic phase is only a small fraction of the initial phenol feed to the first distillation, the treatment cost for the phenol recovery from this organic phase is very small.

More particularly, Applicant has found that by cooling the mixture of phenol and water there is recovered an aqueous phase, which, without any treatment thereof is essentially free of MBF, whereby such aqueous phae may be recycled to the distillation without further treatment.

Moreover, the phenol in the organic phase from such initial distillation may be further distilled in the presence of water to provide a phenol stream, which is suitable for recycle as feed to the initial distillation, and ultimate recovery as high purity phenol.

Furthermore, the aqueous phase recovered from the overhead of the second distillation may be recycled to either the first and/or second distillation, without further purification to remove MBF.

By proceeding in this manner, it is possible to concentrate the MBF and the other impurities present in the initial phenol feed into a smaller quantity of phenol than previously achieved in the art, which thereby reduces the overall cost of the purification by reducing the quantity of phenol which must be subjected to caustic-/acid or other treatment.

The crude phenol, which contains MBF and other impurities, is initially distilled in the presence of water so as to recover as bottom product a separate phenol stream having a reduced quantity of MBF, and other like impurities. Such distillation may be effected at conditions as generally known in the art, with the distillation generally being at either atmospheric, subatmospheric or supreratmospheric pressures as known in the art. If the distillation is performed at atmospheric pressure, the overhead temperature is 99°–101° C. and the bottom temperature is 182°–190° C.

A phenol stream, having a reduced quantity of MBF, and other impurities and free of water, is recovered from a bottom portion of the distillation column.

A phenol-water mixture, including impurities and in particular MBF, is recovered from a top portion of the column, generally as a water-phenol azeotrope. Such water-phenol mixture is separated into an organic phase, comprised of phenol and MBF, and an aqueous phase, comprised of water and phenol, with such phase separation being easily accomplished by cooling the mixture to a temperature at which such phase separation is accomplished. In general, the mixture is cooled to a temperature in the order of from 0° C. to less than 50° C. Such aqueous phase, which includes phenol and water (with the water generally being saturated with phenol) is essentially free of MBF; i.e., the phase contains less than 25 ppm of MBF, and most generally less than 15 ppm of MBF. As a result, such water phase may be recycled to the distillation without further purification thereof. All or a portion of such aqueous phase may be recycled to the distillation, with in most cases, all of such aqueous phase being recycled to the distillation so as to maximize recovery of the phenol. Moreover, such recovered water provides most of the water requirements for the distillation. Only a small stream of make up water is needed to compensate for the water dissolved in the organic phase of the overhead.

The separated organic phase, which is comprised of phenol, MBF, as well as other impurities, and some water, is then introduced into a second distillation tower wherein the phenol is distilled in the presence of water so as to recover a bottom phenol stream which can be recycled as feed to the first distillation. The second distillation may be operated at the conditions hereinabove described with respect to the first distillation.

The phenol stream recovered as bottom product from the second distillation may then be recycled as feed to the first distillation.

The phenol-water mixture, containing MBF, which is recovered from the top of the second distillation tower is then treated, as hereinabove described, with respect to the phenol-water mixture recovered from the first distillation tower; namely, recovery of a separate aqueous phase, comprised of phenol and water, generally saturated with phenol, and a separate organic phase comprised of phenol, MBF and other impurities, and some water. Such overhead from the second distillation tower is generally a phenol-water azeotrope, and the phase separation may be easily accomplished by cooling such overhead to a temperature at which the phases separate.

The water phase, which contains phenol, may be recycled without further purification to at least one of the first and second distillations as required, and in most cases, to both, with the water present in such phase being employed to provide water requirements for the second distillation.

The organic phase from the overhead of the second distillation, which is comprised of phenol, MBF, and other impurities may then be further treated to recover phenol; for example, by conversion to water soluble phenate, and after the impurities have been separated from the aqueous phase, by regenerating phenol by the addition of acid, or by a further distillation in the manner as hereinabove described.

In this manner, it is possible to recover a phenol product as bottoms from the first distillation stage which contains less than 20 ppm, and preferably less than 15 ppm of MBF. Moreover, by proceeding as hereinabove described, it is possible to recover at least 80%, and preferably at least 90% of the crude phenol to the operation as the phenol product recovered from the bottom of the first distillation tower. Thus, in effect, the MBF and other impurities are concentrated into a small amount of phenol, which leaves an increased portion of the initial phenol available for subsequent treatment for production of high purity phenol.

Although the preferred feed is a phenol produced through the cumene route which has been treated with a base, and an acid or acid anhydride, it is to be understood that the present invention is not limimted to such a feed.

The invention will be further described with respect to the following drawing, wherein:

The drawing is a simplified schematic flow diagram of a preferred embodiment of the invention.

Referring now to the drawing, a crude phenol, in line 10, which includes MBF impurity, and which may further include one or more of acetone, alpha-methylstyrene, cumene, acetol and acetophone, and other impurities, is introduced into a top portion of a distillation column, generally designated as 11. Steam or hot oil is used to supply energy to this column through line 12 to a bottom and/or side reboiler. A recycle stream containing phenol and impurities, obtained as hereinafter described, is introduced into the top portion of the column through line 25. Another recycle stream, containing water and dissolved phenol, obtained as hereinafter described, is introduced into the top position of column 11 through line 14.

The column is operated at a temperature and pressure, as hereinabove described, to separate the impurities from the phenol. Phenol having a reduced quantity of MBF, as well as other impurities, and free of water, is recovred from column 11 through line 16. Such phenol generally contains less than 20 ppm of MBF, and is introduced into a further column for recovery of high purity phenol by separating therefrom higher boiling impurities.

A water-phenol vapor mixture, generally present as a water-phenol azeotrope, is recovered from the top of column 11 through line 15, and such a stream includes MBF, as well as other impurities.

The phenol-water mixture in line 15 is cooled to condense the vapors and is introduced into a phase separation zone, schematically generally indicated as 17 wherein the stream is treated to separate and recover, as separate liquid phases, an aqueous phase and an organic phase.

As hereinabove noted, such separation may be conveniently accomplished by cooling the mixture in line 15 to a temperature at which two liquid phases are formed.

An aqueous phase, comprised of phenol and water, with the water generally being saturated with the phenol, and which may include some amounts of impurities including a small amount of MBF, is recovered from separation zone 17 through line 14 for recycle to the first distillation tower 11, as hereinafter described.

An organic phase, which is comprised of phenol, with some water, and which is more concentrated in MBF and possibly other impurities than either of the streams 10 and 25, is recovered from zone 17 through line 19 for introduction into a second distillation tower, schematically generally indicated as 21. An aqueous stream containing phenol and water, obtained as hereinafter described, is introduced into the top portion of the column 21 through line 23. Heat is supplied to column 21 via a bottom or side reboiler, indicated as 22.

Column 21 is operated as hereinabove described to recover a bottom phenol stream, essentially free of water, and containing a reduced amount o MBF and other impurities through line 25. Such phenol, in line 25, may be recycled to the disillation tower 11 as hereinafter described.

A mixture of phenol and water, including MBF and other impurities, generally as a water-phenol azeotrope, is recovered from the top of column 21 through line 26 for introduction into a phase separation zone 27 which is operated similarly to zone 17 so as to recover an aqueous phase and an organic phase. As hereinabove described, an aqueous phase, which includes phenol, generally saturated with phenol, and which includes a small amount of MBF may be recovered for recycle to the distillation operation, with such aqueous phase being recovered through line 28.

In order to compensate for the water which is removed from the system by stream 41 or other losses, makeup water can be added to column 11 through line 18 or to column 21 through line 28 or at any other convenient point in the system.

The various streams entering columns 11 and 21 are introduced in the uppe parts of the columns, separately or together as desired by those familiar with the art. The water introduced in the two columns can be partially or completely in the form of steam.

The organic phase recovered from zone 27, in line 41, which is comprised of phenol, some amounts of water, and is relatively rich in MBF, and other impurities, may then be further treated to recover phenol therefrom; for example, by treatement with an aqueous base, such as sodium hydroxide to provide an aqueous phase, including sodium phenate, which is then separated from an organic phase which includes the MBF and other impurities. Such aqueous phase, including sodium phenate, may then be treated with acid to recover the phenol.

Although the invention has been described with respect to a preferred embodiment in the accompanying drawing, it is to be understood that the scope of the invention is not to be limited to such embodiment. Moreover, such embodiment may be modified within the spirit and scope of the present invention.

The invention will be further described with respect to the following examples; however, the scope of the invention is not be limited thereby:

EXAMPLE 1

Chemically treated phenol (hexamethylenediamine followed by phthalic anhydride) was used as feed in the steam distillation. Distillation was done in a one-inch ID Oldershaw column with 52 trays. Treated phenol and water (in a 2/1 weight ratio) were fed to the 50th tray. The vapors leaving the 52nd tray were condensed and formed the azeotrope overhead. Phenol depicted of MBF was obtained as bottoms product. The overhead was cooled to approximately 25° C. and separated into an organic and an aqueous phase. Table 1 shows a summary of the results. Analyses were performed by gas chromatography.

TABLE 1

| Sample Description | Weight of Sample (g) | Total Impurities in ppm | MBF in ppm |
| --- | --- | --- | --- |
| Feed | 882 (Phenol) + 460 (H$_2$O) | 674* | 102* |
| Bottom Product | 751 | 117 | 11 |
| Overhead (organic) | 14.5 | 17028 | 4108 |
| Overhead (aqueous) | 501.5 | 170 | 23 |

*Concentrations refer to the phenol in the feed.

EXAMPLE 2

A phenol mixture containing approximately 2000 ppm MBF and 7000 ppm total impurities was used as feed to a column identical to that of example 1. Phenol was fed at approxiamtely 150 grams/hour and a ratio of H$_2$O/phenol was 0.52/1. As in example 1, the bottom product was removed continuously from the reboiler and overhead was collected which separated into an organic and an aqueous phase. Table 2 summarizes the results of analysis by gas chromatography.

TABLE 2

| Sample Description | Weight of Sample (g) | Total Impurities in ppm | MBF in ppm |
| --- | --- | --- | --- |
| Feed | 558 (Phenol) + 298 Water | 6830* | 1862* |
| Bottom Product | 513 | 552 | 126 |
| Overhead (organic) | 21 | 97559 | 45457 |
| Overhead (aqueous) | 313 | 165 | 22 |

*Concentrations refer to the phenol in the feed.

The above examples illustrate that it is possible to recycle the water to the distillation column without purification, as with an organic solvent or the like. Moreover, it is possible to concentrate the MBF impurity in a small amount of phenol.

The present invention is particularly advantageous in that it is possible to remove impurities, such as MBF from a crud ephenol, by concentrating such impurities in a small amount of the phenol. In this manner, purification is accomplished while maximizing phenol recovery for ultimate production of high purity phenol.

Numerous modifications and variations of the present invention are possible in light of the above teachings and, therefore, within the scope of the appended claims the invention may be practiced otherwise than as particularly described.

What is claimed is:

1. A process for purifying phenol, comprising:
    distilling a crude phenol containing impurities comprising methylbenzofuran in the presence of water to recover a light fraction comprising a mixture of phenol and water in which impurities are concentrated, and a heavy fraction comprising phenol having a reduced quantity of impurities;
    condensing the light fraction to produce an aqueous phase essentially free of impurities, and an organic phase in which the impurities are concentrated;
    separating the aqueous and organic phase;
    recycling at least a portin of the separated aqueous phase to said distilling;
    further distilling the separated organic phase in the presence of water to recover another light fraction comprising a mixture of phenol and water in which impurities are concentrated and another heavy fraction comprising phenol;
    condensing another light fraction to produce another aqueous phase essentially free of impurities and another organic phase in which impurities are concentrated;
    separating another aqueous phase from another organic phase;
    recycling at least a portion of said another aqueous phase to at least one of said distilling and said further distilling; and
    recycling at least a portion of said another heavy fraction to said distilling.
2. The process of claim 1 wherein all of the aqueous phase is recycled to the distilling and all of the anothe aqueous phase is recycled to the further distilling, and at least 80% of the phenol present in the crude phenol is recovered in the heavy fraction from the distilling.
3. The process of claim 2 wherein the separated aqueous phase contains less than 25 ppm of methylbenzofuran.
4. The process of claim 3 wherein the water present in the light fraction from the distilling and the water present in the another light fraction from the further distilling are each recycled directly to the respective distillings without any other treatment to remove impurities therefrom prior to the recycle steps.
5. The process of claim 4 wherein the light fraction is recovered from the distilling as an azeotrope, and the another light fraction is recovered from the further distilling as an azeotrope.

* * * * *